United States Patent [19]

Naglieri et al.

[11] 4,271,090

[45] Jun. 2, 1981

[54] NOVEL 2-BROMOETHYL TELLURIUM BROMIDES

[75] Inventors: Anthony N. Naglieri, Pine Brook; Nabil Rizkalla, River Vale, both of N.J.

[73] Assignee: Halcon Research and Development Corp., New York, N.Y.

[21] Appl. No.: 88,998

[22] Filed: Oct. 29, 1979

[51] Int. Cl.$^3$ .............................................. C07C 165/00
[52] U.S. Cl. ...................................... 260/550; 260/190; 260/231; 568/652; 568/681
[58] Field of Search ........................................ 260/550

[56] References Cited

U.S. PATENT DOCUMENTS

| | | | |
|---|---|---|---|
| 3,262,969 | 7/1966 | Clark et al. | 260/497 |
| 3,668,239 | 6/1972 | Kollar | 260/497 R |
| 3,689,535 | 9/1972 | Kollar | 260/326.13 R |
| 3,715,388 | 2/1973 | Velbert | 260/497 R |
| 3,715,389 | 2/1973 | Hoch et al. | 260/497 R |
| 3,743,672 | 7/1973 | Kollar | 260/497 A |
| 3,770,813 | 11/1973 | Kollar | 260/497 R |
| 3,778,468 | 12/1973 | Kollar | 260/497 R |
| 3,907,874 | 9/1975 | Harvey et al. | 260/497 R |

OTHER PUBLICATIONS

H. Bell et al., J. Chem. Soc. (1925) p. 1877.
C. Fisher et al., J. Org. Chem., 6, 169 (1941).
H. Arpe et al., Angew. Chem. Internat'l Edit., 10, 73–75 (1971).
M. Ogawa et al., Bull. Chem. Soc. Jap., 43, 496 (1970).
K. Irgolic, Org. Chem. of Tellurium, Gordon & Breach, NY, p. 36.
M. Campos et al., Tetrahed., (1962), 18, 521.
M. Ogawa, Bull. Chem. Soc. Jap., 41, 3031 (1968).
M. Ogawa, Tetrahed., 6, 11–13 (1959).
D. Olson, Tetrahed. Letters, 19, pp. 2053–2058 (1966).
H. Riley et al., J. Chem. Soc., (1932), 2342.
M.Campos et al., Tetrahed. Lett. 6, pp. 11–13 (1959).
W. Farrar et al., J. Chem. Soc. (1945) 11.
W. Cooper, Tellurium, pp. 235–243, Nostrand Reinhold (1971).
C. Frick, JACS, 45, 1795–1799 (1923).

Primary Examiner—Anton H. Sutto
Assistant Examiner—M. C. Eakin
Attorney, Agent, or Firm—William C. Long; David Dick; Jack B. Murray, Jr.

[57] ABSTRACT

The novel bis (2-bromoethyl) tellurium dibromide and 2-bromoethyl tellurium tribromide are prepared by reacting ethylene with a source of tellurium tetrabromide in an inert, non-basic organic solvent under certain temperature conditions and in the substantial absence of molecular oxygen.

7 Claims, No Drawings

NOVEL 2-BROMOETHYL TELLURIUM BROMIDES

BACKGROUND OF THE INVENTION

1. Field of the Invention

This invention relates to organo-metallic compounds and, more specifically, to the composition and preparation of 2-bromoethyl tellurium bromides.

2. Description of the Prior Art

Organo-tellurium compounds are valuable in the preparation of a wide variety of chemicals, and reactions between organic compounds and tellurium compounds to form organo-tellurium have been studied. However, these reactions are not yet completely understood, due to the complexities of tellurium chemistry. Thus, while reactions between tellurium tetrachloride and certain olefins have been reported to result in organo-tellurium compounds, the same reactions have not been found to necessarily occur with tellurium tetrabromide.

C. H. Fisher et al., *J. Org. Chem.*, vol 6, pp. 169–174 (1941) found TeCl$_4$ to react in benzene with cyclohexene and styrene exothermically to form high molecular weight, polymeric products. Addition products between TeCl$_4$ and cyclohexene were identified in M. de Moura Campos, et al., *Tetrahedron Letters* No. 6, pp. 11–13 (1959) and Masao Ogawa, *Bull. Chem. Soc. Jap.* vol. 41, p. 3031 (1968), although these researchers disagreed on the type of addition product obtained. M. de Moura Campos, et al., *Tetrahedron*, vol. 18, pp. 521–526 (1962) found unidentified products and elemental tellurium to be formed in the reaction of TeCl$_4$ with diisobutylene, styrene and 1,4-diphenyl-butadiene-1,3. M. Ogawa, *Bull. Chem. Soc. Jap.*, vol. 41, p. 3031 (1968), M. Ogawa et al., *Bull. Chem. Soc. Jap.*, vol. 43, pp. 496–500 (1970) and H. J. Arpe, et al., *Angew Chem. Internat. Edit.*, vol. 10, pp. 73–75 (1971) found a mixture of organo-halogens to result in the reaction of TeCl$_4$ with butene-1, propylene and ethylene, respectively. For example, TeCl$_4$ was found by Arpe et al., to sluggishly react with ethylene in CCl$_4$ at 20°–60° C. to form a mixture of Cl$_2$Te(CH$_2$CH$_2$Cl)$_2$ and Cl$_3$TeCH$_2$CH$_2$Cl, and Ogawa et al., found a mixture of

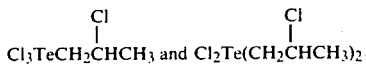

to be formed in the reaction of propylene and TeCl$_4$.

However, W. V. Farrar, et a., *J. Chem. Soc.*, pp. 11–14 (1945) did not obtain β,β'-dihalogen diethyl telluride derivatives by reacting ethylene with TeBr$_4$ in either CCl$_4$ or HBr. Kurt J. Irgolic, *The Organic Chemistry of Tellurium*, (1974) has summarized the art as showing that TeBr$_4$ does not react with ethylene (pp. 36, 172).

Dialkyl tellurium dibromides have been prepared by reacting dialkyl tellurium dinitrates or hydroxy chlorides with HBr, and (CH$_3$)$_2$TeBr$_2$ has been formed by the reaction of a mercuric halide addition compound with NaOH followed by treatment with HBr. *Tellurium*, pp. 235–243 (W. Charles Cooper, et.; Van Nostrand Reinhold Co. 1971).

Inorganic tellurium compounds have been heretofore contacted with ethylene in the presence of carboxylic acid and dissolved bromine in liquid reaction media, e.g., in processes disclosed in U.S. Pat. Nos. 3,262,969; 3,668,239; 3,689,535; 3,715,388; 3,715,389; 3,743,672; 3,770,813; 3,778,468 and 3,907,874, in which the olefin is reacted with a carboxylic acid and molecular oxygen in the presence of a co-catalyst system comprising a variable valent metal cation (e.g., Te) and a halide (e.g., Br) to form ethylene glycol carboxylic acid esters.

Preparation of organo-metallic compounds from olefins and other elements of Group VIA of the Periodic Table, e.g., Se, have also been studied. See, e.g., Carl E. Frick, *J. Amer. Chem. Soc.*, vol. 45, pp. 1795–1799 (1923) (selenium oxychloride+ethylene→bis(β-chloroethyl)selenium dichloride; H. C. Bell, et al., *J. Chem. Soc.*, 1877 (1925) (SeBr$_4$+ethylene→Br$_2$Se(CH$_2$CH$_2$Br)$_2$); H. L. Riley, et al., *J. Chem. Soc.*, pp. 2342–2344 (1932) (ethylene+HCl+SO$_2$→Cl$_2$Se(CH$_2$CH$_2$Cl)$_2$); and D. H. Olson, *Tetrahedron Letters*, No. 19, pp. 2053–2058 (1966) (ethylene+acetic acid+SeO$_2$→ethylene glycol diacetate, bis(β-acetoxy ethyl)selenide and bis(β-acetoxy ethyl)diselenide).

DESCRIPTION OF THE PRIOR ART

Summary of the Invention

According to the present invention, 2-bromoethyl tellurium tribromide and bis(2-bromoethyl)tellurium dibromide are prepared by a process which comprises reacting ethylene with a source of tellurium tetrabromide in liquid medium in the presence of an organic solvent for the reaction at a temperature of less than about 125° and in the substantial absence of molecular oxygen to form the desired bis(2-bromoethyl)tellurium dibromide and 2-bromoethyl tellurium tribromide.

The present invention also provides a process for preparation of nucleophilically-substituted ethane-derivatives by reaction of bis(2-bromoethyl)tellurium dibromide or 2-bromoethyl tellurium tribromide, or mixtures thereof, with a source of the selected nucleophile at elevated temperature optionally in the presence of a solvent for the said tellurium compound.

DETAILED DESCRIPTION OF THE INVENTION

According to this invention ethylene is reacted with a source of tellurium tetrabromide in the presence of a liquid medium containing an inert solvent to prepare novel 2-bromoethyl tellurium bromides. As used herein, the term "2-bromoethyl tellurium bromide" is intended to include bis(2-bromoethyl)tellurium dibromide, 2-bromoethyl tellurium tribromide, and mixtures thereof. Bis(2-bromoethyl)tellurium dibromide can be represented structually as Br$_2$Te(CH$_2$CH$_2$Br)$_2$, and 2-bromoethyl tellurium tribromide can be structurally represented as Br$_3$Te(CH$_2$CH$_2$Br).

The term "source of tellurium tetrabromide" is herein intended to refer to tellurium tetrabromide or a compound or mixtures of compounds such as mixtures of tellurium dioxide and HBr, which, under the conditions of reaction, form tellurium tetrabromide in situ in the reaction zone.

The ethylene reactant can be employed as a liquid or, as is more preferred, as a gas, in which case the ethylene can be introduced as by sparging or by employing any other conventional gas-liquid contacting technique.

Solvents which are suitable for the reaction comprise organic solvents which are inert under the conditions of reaction, with polar solvents being preferred. Exemplary of suitable solvents are aliphatic, aromatic or heterocyclic mono- or polyethers of from 2 to 20 carbon atoms (e.g., tetrahydrofuran, 1,4-dioxane, 1,2-dimethoxyethane, and the like), alcohols of from 1 to 20 carbon atoms (e.g., methanol, tert-butanol, ethanol, and the like), aliphatic, alicyclic or aromatic sulfoxides and sulfones (e.g., dimethyl sulfoxide, and the like), amides of from 2 to 20 carbon atoms (e.g., N,N-dimethyl formamide, N,N-dimethyl acetamide, and the like), nitriles of from 2 to 20 carbon atoms, (e.g., acetonitrile, isobutyronitrile, benzonitrile, and the like), aromatics of from 6 to 24 carbon atoms, (e.g., benzene, toluene, xylenes, and the like), esters of from 2 to 20 carbon atoms, (e.g., ethylene glycol diacetate, and the like), alkanes of from 2 to 20 carbon atoms (e.g., cyclohexane, hexane, octane, and the like), aliphatic halogenated hydrocarbons of from 1 to 20 carbon atoms (e.g., 1,1,2-trichloro-1,2,2-trifluoroethane; and the like), halogenated aromatic hydrocarbons of from 6 to 24 carbon atoms (e.g., monochlorobenzene, dichlorobenzene and trichlorobenzene, and the like), carboxylic acids of from 1 to 20 carbon atoms (e.g., acetic acid, isobutyric acid caproic acid, hexanoic acid and the like).

Preferred as inert solvents in the practice of this invention are aliphatic and aromatic nitriles of up to 7 carbon atoms, aliphatic and cycloaliphatic alcohols of up to 6 carbon atoms, monocarboxylic acids of up to 6 carbon atoms, and aliphatic or aromatic ethers of up to 12 carbon atoms.

The liquid medium for formation of the products of this invention can also contain water provided the temperature which is employed is sufficient to prevent substantial reaction of the water with the desired 2-bromoethyl tellurium bromide. Thus, where water is present, temperatures of less than about 85° C. will generally be used. The concentration of water in the liquid medium is not critical, with concentrations of up to about 95 weight percent of the liquid medium (exclusive of the weight of dissolved $TeBr_4$) being suitable.

Also, the liquid reaction medium is preferably homogeneous, although heterogeneous liquid media can also be employed in the reaction zone.

In the event water is present in the liquid reaction medium, the aqueous liquid is preferably maintained at a pH of not greater than about 4.5, and more preferably at a pH of less than about 4, to avoid substantial decomposition of the tellurium tetrabromide reactant and formation of a $TeO_2$ precipitate. To this end, a suitable acid, such as a lower carboxylic acid, a hydrohalic acid, or mixtures thereof, is preferably employed in the liquid medium in the event water is also present. Especially preferred acids are HBr, acetic acid and formic acid. The amount of such acid will, of course, vary depending on such factors as the particular acid selected, the desired pH to be maintained, and other factors, and can be readily determined by routine experimentation.

The reaction should be performed at a temperature of between the freezing point of the liquid reaction medium and about 125° C., preferably from about 10° to 80° C., and more preferably from about 20° to 50° C. Use of temperatures in excess of about 125° C. is not desired since these higher temperatures prevent the recovery of significant amounts of the desired 2-bromoethyl tellurium bromide. The temperature should be selected within the above ranges to ensure the selected organic solvent remains inert during the course of the reaction.

The pressure at which the process of this invention is performed for obtention of the novel tellurium compound claimed herein is not critical. Obviously, the pressure will be sufficient to maintain a liquid reaction medium. Generally, pressures of from atmospheric to 2,000 psi are quite sufficient, with pressures of from atmospheric to 400 psi being preferred. However, pressures outside these ranges can be used. Therefore, subatmospheric pressures can be employed as can pressures of greater than 2,000 psi, as for example when the process apparatus is capable of withstanding such higher pressures.

The reaction time is not a critical parameter of this invention. The ratio of ethylene to the tellurium tetrabromide source which is used as reactant is also not critical. Generally, ethylene will be employed in an amount which is stoichiometric with the equivalents of tellurium tetrabromide which are used, and more preferably in a molar ratio of ethylene to tellurium tetrabromide equivalents of from about 1:1 to 120:1, more preferably from about 1:1 to 10:1. As used herein, the term "tellurium tetrabromide equivalents" is intended to refer to the moles of $TeBr_4$ which are either added to, or formed in situ, in the reaction zone.

When a mixture of tellurium dioxide and HBr is employed as the source of the tellurium tetrabromide, the molar ratio of HBr to tellurium dioxide is preferably at least about 2:1 and more preferably from about 4:1 to 40:1.

When the partial pressure of ethylene above the liquid phase is not sufficient to maintain the desired pressure in the reaction zone, an inert gas such as nitrogen, argon or the like can be introduced to the reaction zone, such as by admixing the inert gas with the ethylene reactant being charged to the reaction zone.

The reaction of the ethylene and tellurium tetrabromide is exothermic, and conventional means for cooling the reaction vessel can be provided to control the reaction temperature conditions.

The manner in which the ethylene and tellurium tetrabromide source is contacted is not critical. In one embodiment, the tellurium tetrabromide is dissolved or suspended in the selected inert organic solvent and the ethylene is contacted in gas form with the liquid reaction medium, preferably with agitation of the liquid medium. As indicated above, gas sparging or other conventional gas-liquid contacting techniques can be employed to bring the gaseous ethylene into contact with the liquid medium. The degree of agitation is not critical, although substantially turbulent agitation is preferred.

The process of this invention can be practiced in a batchwise, continuous or semi-continuous manner. In the continuous practice of this invention, a solution or slurry of the selected tellurium tetrabromide source can be continuously fed to a reactor, for example a stirred pressure vessel, into which gaseous ethylene is sparged, and from which a liquid product mixture containing the desired 2-bromoethyl tellurium bromide is continuously withdrawn.

The process of this invention is conducted in the "substantial absence of molecular oxygen", that is the ratio of the moles of free molecular oxygen to the moles of Te in the reaction zone should not be greater than 0.5:1 and the ratio of the moles of free molecular oxygen to the moles of ethylene fed to the reaction zone should be less than about 1:1000. The substantial absence of molecular oxygen is important to avoid explosive hazards associated with the handling of oxygen/ethylene gas mixtures and to limit the formation of undesired oxidation by-products.

The bis(2-bromoethyl)tellurium dibromide and 2-bromoethyl tellurium tribromide products can be recovered from the liquid mixture by evaporation of the solvent to dryness to form a mixture of the 2-bromoethyl tellurium bromide crystals and any unreacted tellurium tetrabromide solids. These evaporation techniques are conventional and include use of vacuum distillations and/or use of gas stripping with inert gases sparged into the liquid. To minimize contamination of the 2-bromoethyl tellurium bromide with unreacted tellurium tetrabromide, the solvent is preferably only partially evaporated (desirably, not more than about 80% of the original solvent is evaporated) until a majority of the desired 2-bromoethyl tellurium bromide crystals are formed. The remaining liquid can be recycled to the reaction zone. Alternatively, the reaction mixture withdrawn for product recovery can be chilled, e.g., to a temperature of below about 10° C., to cause formation and precipitation of the desired 2-bromoethyl bromide crystals. The solid product formed in any of the above methods can be separated from any remaining liquid by any standard technique, such as filtration, centrifugation or allowing the solids to settle and decanting the liquid. The 2-bromoethyl tellurium bromide product can be further purified by recyrstallization using conventional techniques from any of the above inert organic solvents which can be employed in the reaction zone.

A mixture of bis(2-bromoethyl)tellurium dibromide and 2-bromoethyl tellurium tribromide will be generally formed by the process of this invention. The formation of bis(2-bromoethyl)tellurium dibromide is, however, favored over the tribromide compound when the ethylene reactant is employed in an excess of that stoichiometrically required to form the dibromide compound, that is, in a mole ratio of ethylene to the tellurium tetrabromide of at least 2:1. Correspondingly, formation of 2-bromoethyl tellurium tribromide is favored when the ethylene to tellurium tetrabromide molar ratio is less than 2:1.

Use of The Novel Compounds

According to the present invention, the novel bis(2-bromoethyl)tellurium dibromide and 2-bromoethyl tellurium tribromide products of this invention can be reacted, preferably in a liquid medium which can be aqueous or non-aqueous, with a source of a selected nucleophile to form the corresponding nucleophilically-substituted ethane-derivative.

The term "nucleophilic substituent" is intended to refer to negatively charged ions and other groups rich in negative charges, i.e., having at least one unshared pair of electrons capable of displacing at least one tellurium-carbon bond from the foregoing tellurium-ethylene bromide compounds of this invention. As used herein, the term "nucleophile source" is intended to refer to those nucleophilic reactants which contain at least one such nucleophilic substituent or which function as a source of such nucleophile in the reaction zone under reaction conditions.

Exemplary of nucleophilic substituents useful in the present invention are members selected from the group consisting of —OH, —CN, —NH$_2$, —NRR', —NHR, —SH, —SR, —OR, —Cl, —F, —I, —Br, and

and mixtures thereof, wherein R and R' are the same or different and are each organic moieties and are preferably members independently selected from the group consisting of alkyl, nitroaryl, aryl, cycloalkyl, aralkyl, alkaryl and heterocyclic. Preferred are nucleophilic substituents selected from the group consisting of —OH, —OR, —Cl, —F, —I, —Br and

wherein R is as defined above.

When either "R" or "R'" is alkyl, the alkyl group can be branched or straight-chained and generally contains from 1 to 12 carbon atoms, and preferably contains from 1 to 6 carbon atoms. Examples of such alkyl groups are methyl, ethyl, isopropyl, pentyl, octyl and dodecyl. When either "R" or "R'" is cycloalkyl, the cycloalkyl group generally contains from 3 to 12 carbon atoms, and preferably contains from 4 to 8 carbon atoms. Examples of such groups are cyclopropyl, cyclobutyl, cyclohexyl, cyclooctyl and cyclododecyl. When either "R" or "R'" is alkaryl, the aryl component generally consists of phenyl or tolyl and the alkyl component generally has from 1 to 12 carbon atoms, and preferably from 1 to 6 carbon atoms. Examples of such alkaryl groups are tolyl, m-ethylphenyl, o-ethyltolyl and m-hexyltolyl. When "R" or "R'" is aralkyl, the aralkyl group generally consists of phenyl or alkyl-substituted phenyl as the aryl component and an alkyl component having from 1 to 12 carbon atoms and preferably from 1 to 6 carbon atoms. Examples of such aralkyl groups are benzyl, o-ethylbenzyl and 4-isobutyl benzyl. When either "R" or "R'" is aryl or nitroaryl, the aryl group is generally phenyl.

When either "R" or "R'" is heterocyclic, the heterocyclic group generally consists of a compound having at least one ring of 6 to 12 members in which one or more carbon atoms is replaced by oxygen or nitrogen. Examples of such heterocyclic groups are furyl, pyranyl, pyridyl, piperidyl, dioxanyl, tetrahydrofuryl, pyrazinyl and 1,4-oxazinyl.

The selected nucleophilic substituent is supplied to the reaction zone as a source of a nucleophile, which is preferably soluble in the selected liquid medium, where a liquid is employed in the reaction zone. When the selected nucleophilic substituent to be introduced to the ethane compound is hydroxy (—OH), the source of this nucleophile will generally comprise a member selected from the group consisting of water, alkali metal hydroxides, alkaline earth metal hydroxides, ammonium hydroxide, quaternary ammonium hydroxides and mixtures thereof. Exemplary of alkali metal and alkaline earth metal hydroxides are potassium hydroxide, sodium hydroxide, lithium hydroxide, calcium hydroxide, barium hydroxide and magnesium hydroxide. When the selected nucleophilic substituent comprises cyanide (—CN), the source of the cyanide group will generally comprise a member selected from the group consisting of alkali metal cyanides, alkaline earth metal cyanides, ammonium cyanide, quaternary ammonium cyanides and mixtures thereof. Exemplary of such sources of cyanide are sodium, potassium, lithium, barium and magnesium cyanides. When the selected nucleophilic substituent is —OR, wherein "R" is as defined above, the source of such ether groups will generally comprise a member selected from the group consisting of alcohols having the formula ROH, wherein "R" is as defined above, alkali metal and alkaline earth metal salts of such alcohols and mixtures thereof. Examples of such sources of —OR nucleophiles are the alkanols of 1 to 12 carbon atoms, preferably of 1 to 6 carbon atoms (such as methanol, ethanol, isopropanol, isobutanol and 2-hexanol), phenol, benzyl alcohol, m-tolyl alcohol, m-ethyl phenol, 2-ethyl-3-methyl-hydroxy toluene, 3-hexyl-5-methyl-hydroxy toluene, cyclohexanol, 3-hydroxy pyridine and 2-hydroxy furan and alkali metal and alkaline earth metal salts of the foregoing, such as sodium methoxide, potassium ethoxide, sodium phenoxide and potassium benzoxide.

When the selected nucleophilic substitutent is —SR, wherein "R" is as defined above, the source of the —SR group will generally comprise a member selected from the group consisting of mercaptans having the formula RSH, wherein "R" is as defined above and alkali metal, alkaline earth metal, ammonium and quaternary ammonium salts thereof. Exemplary of such mercaptans are methyl mercaptan, ethyl mercaptan, and ammonium, sodium and potassium salts thereof. When the selected nucleophilic substituent is —SH, the source of this nucleophile will generally comprise a member selected from the group consisting of quaternary ammonium hydrosulfides, ammonium hydrosulfide, alkali metal hydrosulfides, alkaline earth metal hydrosulfides and mixtures thereof. Exemplary of such sources of —SH are tetramethyl ammonium hydrosulfide, tetraethyl ammonium hydrosulfide, sodium hydrosulfide, potassium hydrosulfide and calcium hydrosulfide. When either F—, Cl—, I— or Br— is the selected nucleophilic substituent, the source of such nucleophile will generally comprise a member selected from the group consisting of the corresponding ammonium halide, hydrogen halide, alkali metal and alkaline earth metal halide, quaternary ammonium halide or transition metal (e.g., copper) halide. Examplary of such sources of halides are sodium chloride, potassium chloride, sodium fluoride, potassium fluoride, HF, HBr, HCl, HI and the like.

When —NH$_2$ is selected nucleophilic substituent, the nucleophile source will generally comprise a member selected from the group consisting of ammonia, compounds which liberate NH$_3$ in basic aqueous media and mixtures thereof. Ammonia can be employed as a gas or liquid. Where gaseous ammonia is used, any gas containing NH$_3$ may be employed.

When —NHR or —NRR' is the selected nucleophilic substituent, the nucleophile source will comprise the corresponding primary or secondary amine having the formula HN$_2$R and

respectively, wherein "R" and "R'" are as defined above. Examples of such primary amine nucleophile sources are NH$_2$CH$_3$, NH$_2$CH$_2$CH$_3$, aniline, isobutyl amine, and cyclohexylamine. Examples of such secondary amine nucleophile sources are methyl ethylamine,
di-n-butylamine, diphenylamine, dicyclopentyl amine, and dibenzyl amine.

When

is the selected nucleophilic substituent, the nucleophile source will comprise the corresponding carboxylic acid having the formula

or carboxylic acid anhydride having the formula RC(O)—O—C(O)R, wherein "R" is as defined above. Examples of such nucleophile sources are acetic acid, benzoic acid, propionic acid, toluic acid, p-nitro-benzoic acid, butyric acid, isobutyric acid, acetic anhydride, propionic anhydride and the like.

As will be apparent from the foregoing, so long as the compound chosen as the nucleophile source functions in the reaction zone under reaction conditions to provide the selected nucleophilic substituent which is to be substituted on the ethane compound to displace the C-Te bond, there is not criticality as to the selection of the nucleophile source.

From the foregoing, it will be apparent that the nucleophilically-substituted ethane-derivatives of this invention comprise mono- and di-substituted ethane compounds of the formula (IV):

$$X_1-CH_2CH_2-X_2 \qquad (IV)$$

wherein $X_1$ and $X_2$ are independently selected from the group consisting of —OH, —CN, —NH$_2$, —NRR', —NHR, —SH, —SR, —OR, —Cl, —F, —I, —Br, and

and mixtures thereof, wherein R and R' are the same or different and are as defined above.

Exemplary of nucleophile-substituted ethane derivatives prepared from a 2-bromoethyl tellurium bromide according to this invention are di-substituted ethanes such as 1,2-dibromoethane, 1,2-dihydroxy ethane (ethylene glycol), 1,2-dicyano ethane, ethylene diamine, 1,2-bis(dimethylamino) ethane, 1,2-bis (N-phenylamino) ethane, 1,2-bis (N-tolylamino) ethane, HSCH$_2$CH$_2$SH, H$_2$CSCH$_2$CH$_2$SCH$_3$, H$_5$C$_2$φSCH$_2$CH$_2$SφC$_2$H$_5$, H$_5$C$_2$OCH$_2$CH$_2$OC$_2$H$_5$, (CH$_3$)$_2$CHOCH$_2$CH$_2$OCH(CH$_3$)$_2$, φOCH$_2$CH$_2$Oφ, the 1,2-dichloro, 1,2-difluoro and 1,2-diiodo ethanes, CH$_3$CO$_2$CH$_2$CH$_2$O$_2$CCH$_3$, 1,2-dicyclopropyloxy ethane, CH$_3$(CH$_2$)$_2$CO$_2$CH$_2$CH$_2$O$_2$C(CH$_2$)$_2$CH$_3$, and mono-substituted bromoethanos such as 1-hydroxy-2-bromoethane, 1-cyano-2-bromoethane, 1-amino-2-bromoethane, 1-dimethyl-amino-2-bromoethane, 1-N-phenylamino-2-bromoethane, 1-N-tolylamino-2-bromoethane, HSCH$_2$CH$_2$Br, CH$_3$SCH$_2$CH$_2$Br, C$_2$H$_5$φSCH$_2$CH$_2$Br, C$_6$H$_{13}$OCH$_2$CH$_2$Br, (CH$_3$)$_2$CHCH$_2$OCH$_2$CH$_2$Br, φOCH$_2$CH$_2$Br, the 1-chloro-, 1-fluoro- and 1-iodo-2-bromoethanes, (CH$_3$)$_2$CHCO$_2$CH$_2$CH$_2$Br, NO$_2$φOCH$_2$CH$_2$Br,

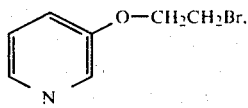

1-cyclohexylamino-2-bromoethane, ethylene glycol diacetate (i.e., $CH_3C(O)OCH_2CH_2O(O)CCH_3$), 2-bromoethyl acetate (i.e., $CH_3C(O)OCH_2CH_2Br$), and the like.

Of course, it will be understood that the selected 2-bromoethyl tellurium bromide which is employed as reactant can itself comprise a source of a bromine nucleophile to form ethane compounds of the above formula IV herein one or more of the $X_1$ and $X_2$ are bromine.

In the preferred embodiment of the process of the present invention, the selected tellurium-ethyl bromide compound and source of the nucleophile are contacted in the liquid phase in the reaction zone. The liquid medium selected for use can comprise (1) one or more of the reactants (when a liquid reactant is employed) or (2) a solvent for the selected tellurium-ethyl bromide compound and/or for the nucleophile source. The choice of such solvent will, of course, vary widely and will depend on the type of reactor vessel used, the temperature and pressure selected and other factors. Generally, however, suitable solvents include aromatic, aliphatic and cycloaliphatic hydrocarbon solvents, such as benzene, toluene, xylene, cyclopentane, cyclooctane, cyclohexane, pentane, octane, heptane and the like. The selected solvent is preferably one which does not react adversely with any component of the system to depress yields of the desired product, though the solvent can comprise the nucleophile source in the event the latter is a liquid under reaction conditions. The amount of solvent employed is not critical.

While both the tellurium-ethyl bromide compound and nucleophile source will preferably be soluble in the selected liquid media, this is not critical and liquid media in which the Te-ethyl bromide compound, nucleophile source or both are either insoluble or only slightly soluble can also be employed.

The manner of contacting the 2-bromoethyl tellurium bromide compound and nucleophile source in the reaction zone is not critical, and the process can be performed in a batchwise, continuous or semi-continuous manner. Thus, a single reaction zone or a plurality of reaction zones in series or parallel can be employed, and the 2-bromoethyl tellurium bromide compound and nucleophile source, and solvent or inert liquid (if any) can be fed to the reaction zone separately or as one or more combined stream. As indicated previously, ammonia can be fed to the reaction zone either as a gas or liquid.

The relative amounts of the 2-bromoethyl tellurium bromide and nucleophile source fed to the reaction zone are not critical. However, it is preferable to employ the nucleophile source in an amount at least equal to the quantity which is stoichiometrically required to react with the quantity of 2-bromoethyl tellurium bromide compound introduced for reaction. Thus, the molar ratio of the nucleophile source to bis (2-bromoethyl) tellurium dibromide is preferably at least about 2:1, and the molar ratio of the nucleophile source to 2-bromoethyl tellurium tribromide is preferably at least about 1:1. (These molar amounts of the nucleophile source are based on the equivalents of nucleophilic substituent in each mole of nucleophile source.)

The formation of such products from the 2-bromoethyl tellurium bromide of this invention can be carried out over a wide range of temperatures. Temperatures, for example, from 100° to 300° C. are suitable, with temperatures from about 120° C. to 200° C. being preferred. Temperatures as low as 50° C. can be used but they tend to lead to reduced reaction rates. Higher temperatures than those mentioned can be employed, but there is no particular advantage to such practice.

The process of this invention can also be carried out over a wide range of pressures, with a choice of pressure being dictated only by economics. In the preferred liquid phase embodiment, the pressure above the liquid phase should be sufficient to maintain at least part of the 2-bromoethyl tellurium bromide and nucleophile source in the liquid phase. Pressures will normally range from 0.1 to 2000 atmosphere gage, although higher or lower pressures may also be used. For example, while pressures of greater than 2000 atmospheres gage can be used, there is little advantage to their use and a substantial economic penalty would be incurred as a result of the increased cost of equipment capable of withstanding such higher pressures.

Reaction time is not a significant parameter of the process of this invention, depending to a large extent upon the temperature employed as well as upon reactant concentrations. Suitable reaction times (i.e., times sufficient for the 2-bromoethyl tellurium bromide/nucleophile source reaction to occur) for the liquid phase embodiment will normally be within the range of 0.1 to 100 hours. Reaction time in a batch system is self-explanatory. In a continuous system, the residence time is defined as the quotient obtained by dividing the volume of the liquid phase reaction medium within the reaction zone by the rate (in consistent volume units per hour) at which the 2-bromoethyl tellurium bromide, solvent and nucleophile source (both fresh feed and any recycled material) is introduced to the reaction zone.

The zone in which the reaction of the 2-bromoethyl tellurium bromide and nucleophile source is effected in accordance with the process of the present invention can comprise one or more autoclaves or an elongated tubular zone or series of such zones. Of course, reaction zone construction should be such that the reaction zone can withstand reaction temperature and pressure and should be fabricated from materials relatively inert to reaction with the components of the reaction mixture. Suitable inert materials for reaction zone construction include titanium, tantalum, zirconium, various stainless steels, the Hastelloys, and the like. The reaction zone is also suitably fitted with appropriate temperature control devices. Suitably the reaction zone is configured to provide sufficient agitation to ensure adequate contact between the reactants. Any convenient agitation means known to those skilled in the art can be used, including vibration, shaking, stirring, etc., as illustrative techniques. A gaseous reactant, such as gaseous ammonia, if employed, would normally be introduced at a point within the reaction zone below the level of the liquid phase reaction medium maintained therewithin in order to facilitate agitation and adequate contact by gas-sparging techniques.

The nucleophilically substituted ethane-derivative produced by the process of the present invention can be recovered from a liquid medium by conventional methods. Thus, the liquid medium can be subjected to conventional distillation processes to recover the product nucleophilically-substituted ethane derivative therefrom. Unreacted 2-bromoethyl tellurium bromide compound and nucleophile source can be recovered from the reaction zone by conventional methods and can be recycled to the process. Likewise, solvent recovered from a liquid medium and promoter (where employed) can also be recycled to the process.

The reaction of the selected nucleophile source and the selected 2-bromoethyl tellurium bromide compound will result in the formation of reduced tellurium species, such as divalent tellurium salts. Where desired, these reduced tellurium species can be recovered from the liquid reaction medium by conventional methods and reoxidized to the tetravalent state for recycle to the step in which the 2-bromoethyl tellurium bromide compound is formed. The method by which the reduced tellurium species are oxidized to the tetravalent state is not critical to the present invention and can include any of the conventional methods for oxidizing this or similar metals.

The foregoing reactions of the 2-bromoethyl tellurium bromides and nucleophile sources to form any of the above-described nucleophilically-substituted ethane-derivatives of this invention do not require the presence of molecular oxygen and thus can be carried out in the substantial absence of free molecular oxygen, i.e., at molar ratios of $O_2$ to tellurium (calculated as the metal) in the reaction zone of less than about 0.5:1.

In a particularly preferred embodiment of the process of this invention the selected 2-bromoethyl tellurium bromide is introduced to a reaction zone wherein the 2-bromoethyl tellurium bromide is reacted in liquid medium with a carboxylic acid selected from the group consisting of mono- and di-basic acids having up to 30 carbon atoms per molecule to form ethylene glycol esters of the carboxylic acid. The carboxylic acid is preferably a lower mono-aliphatic acid of from 2 to 6 carbon atoms such as acetic, propionic, butyric, isobutyric, the valeric and carproic acids, as well as their substituted derivatives. Preferably, any substituents are inert under the reaction conditions.

In the formation of such ethylene glycol esters, the liquid medium in the reaction zone is preferably maintained at a temperature of at least about 100° C. up to about 300° C., and more preferably from about 120° to 200° C. Pressure and reaction time are as discussed previously.

The process of this invention can be further illustrated by reference to the following examples, wherein parts are by weight unless otherwise indicated.

EXAMPLE 1

To a 200 cc pressure vessel is charged 3.5 parts of tellurium tetrabromide and 50 parts of acetonitrile. The resulting liquid mixture is magnetically stirred under an atmosphere of ethylene (400 psig) for three hours at a temperature of 25° C. At the end of this time, the liquid reaction mixture, which comprises a clear amber-colored effluent, is placed under a nitrogen gas stream at room temperature to permit evaporation of the acetonitrile solvent. Well formed yellow crystals are observed upon evaporation of 70 wt. % of the solvent. 2.5 Parts of these crystals are isolated for detailed physical, chemical and spectral identification as follows:

(1) The crystals are determined to have a melting point of from 119° to 120° C., employing a capillary tube.

(2) Elemental analysis shows that the crystals contain 25 weight percent tellurium, 9.6 weight percent carbon, 1.57 weight percent hydrogen and 64 weight percent bromine, compared with theoretical values of 25.4 weight percent tellurium, 9.5 weight percent carbon, 1.6 weight percent hydrogen and 63.5 weight percent bromine for the empirical formula $TeC_4H_8Br_4$.

(3) Polargraphic analysis using differential pulse polarogram shows that the crystals contain 23.4 percent by weight tetravalent tellurium.

(4) A sample of the crystals are contacted with an excess of silver nitrate in a liquid medium comprising 77 vol. % glacial acetic acid and 23 vol. % 1 M. nitric acid to precipitate silver bromide. Weighing of the silver bromide precipitate shows the crystals to have contained 32 percent by weight of ionizable $Br^-$, which is 50% of the total Br content of the sample. This establishes that one-half of Br atoms in the crystals are bound to tellurium and that the other Br atoms are bound to carbon atoms.

(5) Infrared spectroscopy in Nujol and KBr shows absorption peaks at 700 $cm^{-1}$ which corresponds to $CH_2$ or CBr bonds, 635±5 $cm^{-1}$ which lies in the frequency region of CBr bond stretch and 430 $cm^{-1}$ which indicates the presence of C—Te bond.

(6) Mass spectral evaluation by acquiring standard 75 eV spectra of the sample vaporized directly into the ion source shows a distinctive isotopic distribution of tellurium and bromine compounds. The highest isotopic cluster which is discerned is M/e 417 to 429, and the masses and abundance ratios are as predicted for

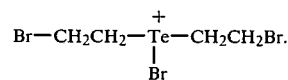

Isotopic M/e 107 and 109 indicate the presence of —$CH_2CH_2Br$ group in the molecule. Isotopic clusters of M/e 392-396, 280-290, and 230-240, which correspond to $Br_2$—$Te^+$—$CH_2CH_2Br$, $Te^+Br_2$ and $BrTe^+$—$CH_2CH_2Br$, respectively, are also obsreved.

(7) Proton NMR analysis using 100 MHZ NMR spectrum indicates non-equivalence of protons. A carbon-13 NMR spectrum shows two singlets at δ44.93 and δ28.02 of equal intensities (δ45=Te—C bond; δ28=Br—CH$_2$—CH$_2$—).

The foregoing analysis confirm the structure of the crystals as:

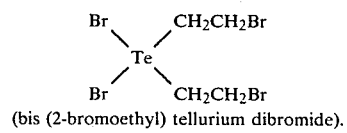
(bis (2-bromoethyl) tellurium dibromide).

EXAMPLE 2

Using the procedure of Example 1, six parts of tellurium tetrabromide, four parts of 48% HBr and 46 parts of acetic acid are charged to the pressure vessel. Ethylene gas is bubbled through the mixture for three hours at 25° and atmospheric pressure. The liquid effluent is then charged to a roto-evaporator under 1 mmHg pressure and at 20° C. to evaporate 98 wt. % of the solvent. The solids thus formed are recovered and subjected to the following analyses:

(1) Elemental analysis of the residue obtained as above shows that the residue contains 19.5 weight percent tellurium, 4.88 weight percent carbon, 1.42 weight percent hydrogen and 65.8 weight percent bromine, compared with the theoretical distributions of 26.8 weight percent tellurium, 5.1 weight percent carbon, 0.8 weight percent hydrogen and 67.3 weight percent bromine for the empirical formula $TeC_2H_4Br_4$.

(2) Employing the silver nitrate precipitation method as described in Example 1, the residue is found to contain 51% by weight of ionizable $Br^-$, which is 78 weight percent of the total Br content of the residue. This establishes that three-fourths of the Br atoms in the solids are bound to tellurium and that one-fourth of the Br is bound to a carbon atom.

The solids thus recovered are therefore found to contain a compound of the structural formula:

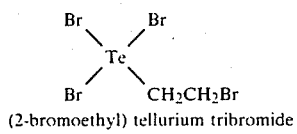

(2-bromoethyl) tellurium tribromide

EXAMPLE 3

1.0 part of the crystals of bis (2-bromoethyl) tellurium dibromide obtained as in Example 1 is charged with 20 parts of glacial acetic acid to a pressure vessel. The mixture is heated with stirring under 400 psig argon atmosphere for three hours at 150° C. Analysis by gas chromatography shows the liquid reaction mixture, at the completion of the above time, to contain 1,2-dibromoethane, 2-bromoethyl acetate and ethylene glycol diacetate in yields of about 1.0 mole %, 102 mole % and 103 mole %, respectively, based on the moles of tellurium in the 2-bromoethyl tellurium bromide which is charged.

EXAMPLE 4

A sample (1 part) of the solids obtained as in Example 2 is charged with 20 parts of glacial acetic acid to a pressure vessel. This mixture is then heated with stirring under 400 psig of argon atmosphere for three hours at 150° C. Gas chromatographic analysis of the effluent indicates the presence of 2-bromoethyl acetate and ethylene glycol diacetate in yields of about 33.1 mole % and 65 mole %, respectively, based on the moles of Te charged as 2-bromoethyl tellurium tribromide.

EXAMPLE 5

The procedure of Example 1 is repeated in separate runs employing 5.25 parts of $TeBr_4$ together with 75 parts of acetonitrile, using the pressures, times and temperatures shown in Table I below. The amount of bis (2-bromoethyl) tellurium dibromide thereby produced is also shown in Table I.

TABLE I

| Run No. | Ethylene Pressure (psig) | Time (min.) | Temp. (°C.) | Product* (parts) |
|---|---|---|---|---|
| 1 | 100 | 5 | 56 | 3.6 |
| 2 | 400 | 5 | 6 | 2.6 |
| 3 | 800 | 20 | 20 | 4.2 |

*Bis(2-bromoethyl) tellurium dibromide

EXAMPLE 6

Following the procedure of Example 1, 4.5 parts of tellurium tetrabromide, 1.0 part of 48% aqueous HBr and 50 parts of chloroform are charged to the reaction vessel. Gaseous ethylene is then bubbled at atmospheric pressure through the liquid reaction medium at a temperature of 25° C. for three hours. Chloroform is added as needed to replace any chloroform evaporated by passage of the gases therethrough, thereby maintaining the selected liquid volume. At the end of this time, the liquid is withdrawn from the reaction zone and subjected to distillation at a pressure of 1 mmHg and at 25° C. for three hours to remove all solvent and water, thereby forming 1.8 parts of a residue after three hours. A 1 part sample of the residue is removed and dissolved in 20 parts of acetonitrile, which is then, by the foregoing distillation technique, evaporated to about 80% of its initial volume. The crystals which are formed are withdrawn and found to comprise bis (2-bromoethyl) tellurium dibromide. The remainder of the residue produced in the first distillation is then contacted with 30 parts of acetic anhydride with stirring at a temperature of 150° C. for three hours under an atmosphere of 400 psig argon. At the end of this reaction time, solids which are formed are allowed to settle and a sample of the liquid mixture is subjected to analysis by gas chromotography. 2-Bromoethyl acetate and ethylene glycol diacetate are found to be present in a yield of about 13 mole % and 102 mole %, respectively, based on the moles of Te charged as the 2-bromoethyl tellurium bromide.

EXAMPLE 7

The procedure of Example 6 is repeated except that the charge to the reaction vessel comprises three parts tellurium tetrabromide, five parts of 48% aqueous HBr and 20 parts benzonitrile. Following isolation of 5 parts of residue by distillation of the reaction mixture as in Example 6, and confirmation of the presence of bis (2-bromoethyl) tellurium dibromide in the residue, 1 part of the residue is contacted with 20 parts of acetic anhydride under the conditions of Example 6. Thereafter, the reaction effluent is found to contain 2-bromoethyl acetate and ethylene glycol diacetate in yields of about 15 mole % and 175 mole %, respectively, based on the moles of Te charged as the 2-bromoethyl tellurium bromide.

EXAMPLE 8

To illustrate the use of tellurium tetrabromide formed in situ in the reaction zone to prepare 2-bromoethyl tellurium bromides of this invention, the procedure of Example 1 is repeated except that the charge to the reaction vessel comprises three parts tellurium dioxide, eight parts of 48% aqueous HBr and 42 parts of glacial acetic acid. The mixture is allowed to react with stirring at 25° C. for a period of three hours under a pressure of 400 psig ethylene. At the end of this reaction time, the liquid effluent is filtered to remove unreacted tellurium dioxide solids and the resulting liquid is distilled as in Example 2 for removal of solvent and water. A sample of the resulting residue is analyzed and found to contain, after recrystallization, a mixture of bis (2-bromoethy) tellurium dibromide and 2-bromoethyl tellurium tribromide. A 1 part portion of the residue is then reacted with 20 parts of glacial acetic acid at a temperature of 150° C. with stirring for three hours under an atmosphere of 400 psig argon. At the end of this time, the liquid effluent is analyzed and is found by gas chromotography to contain 2-bromoethyl acetate, ethylene glycol diacetate and 1,2-dibromoethane in yields of about 5.1 mole %, 29.2 mole % and 130 mole %, respectively, based on the moles of Te charged as the 2-bromoethyl tellurium bromide.

EXAMPLE 9

Using the procedure of Example 1, a mixture comprising seven parts tellurium tetrabromide, eight parts 48% aqueous HBr and 42 parts glacial acetic acid are charged to the reaction vessel and are reacted for three hours at 25° C. using an ethylene pressure of 800 psig. A sample of the liquid effluent from the reaction zone, withdrawn after the three hours of reaction, is subjected to analysis by gas chromotography and no detectable amount of any glycol derivative (i.e., no detectable peak corresponding to a —CH—CH— group substituted by either —OH, Br or acetate groups) is found. The effluent withdrawn from the reaction vessel is then passed to a separate 200 cc reaction vessel and is heated under 400 psig of argon for three hours at 150° C. At the end of this time, gas chromatographic analysis of the liquid effluent indicates the presence of 1,2-dibromoethane, 2-bromoethyl acetate and ethylene glycol diacetate in yields of about 7.3 mole %, 39.2 mole % and 76.1 mole %, respectively based on the moles of Te charged as the 2-bromoethyl tellurium bromide.

EXAMPLE 10

Using the same charge of tellurium tetrabromide, aqueous HBr and glacial acetic acid employed in Example 9, and contacting this mixture under the same conditions as in Example 9 with gaseous ethylene, an effluent is withdrawn from the reactor after the three hours of reaction time at 25° C. The reaction effluent is then distilled using the distillation technique of Example 2 (1 mmHg at 25° C.) in a stepwise manner. First, the liquid is distilled to remove 90 wt. % of the acetic acid, and solids are observed to be formed. A sample of these solids is then withdrawn and upon analysis is found to comprise bis (2-bromoethyl) tellurium dibromide. A sample of the remaining liquid is also taken and analyzed and is found to contain both bis (2-bromoethyl) tellurium dibromide and 2-bromoethyl tellurium tribromide. The liquid remaining following the first stage of distillation is, using the same distillation method, distilled to dryness. This residue is then admixed with 30 parts of glacial acetic acid and is heated with stirring at 150° C. for three hours to react the 2-bromoethyl tellurium bromides in the residue with the acetic acid. At the end of this reaction time, gas chromatographic analysis of the liquid reaction effluent indicates 2-bromoethyl acetate and ethylene glycol diacetate to be formed in yields of about 17 mole %, and 125 mole %, respectively, based on the moles of Te charged as the 2-bromoethyl tellurium bromide.

EXAMPLE 11

The procedure of Example 9 is repeated except that the charge to the reactor comprises six parts tellurium tetrabromide and 50 parts glacial acetic acid and the mixture is contacted with 400 psig ethylene at 25° C. for three hours. The reaction effluent is found to contain both bis (2-bromoethyl) tellurium dibromide and 2-bromoethyl tellurium tribromide. An atmosphere of argon, 400 psig is then placed over the liquid which is then heated at a temperature of 150° C. for three hours as in Example 9. Gas chromatographic analysis of the liquid at the end of this second reaction period indicates that 2-bromoethyl acetate and ethylene glycol diacetate are formed in yields of about 15.6 mole % and 99.5 mole %, respectively, based on the moles of Te charged as the 2-bromoethyl tellurium bromide.

EXAMPLE 12

The procedure of Example 9 is repeated except that the mixture of tellurium tetrabromide, aqueous HBr and glacial acetic acid which is charged to the reaction vessel is reacted with ethylene (400 psig) for 30 minutes at a temperature of 10° C. At the end of this 30 minutes reaction time, the reaction mixture is found to contain both bis (2-bromoethyl) tellurium dibromide and 2-bromoethyl tellurium tribromide. The reaction mixture is then heated for three hours at 150° C. in an atmosphere of argon (400 psig). At the end of this time gas chromatographic analysis of the effluent indicates a presence of 2-bromoethyl acetate and ethylene glycol diacetate in yields of about 20 mole % and 79 mole %, respectively, based on the moles of Te charged as the 2-bromoethyl tellurium bromide.

EXAMPLE 13

The procedure of Example 12 is repeated except that the initial charge to the reaction vessel is heated at a temperature of 65° C. for 30 minutes. Again, the reaction effluent is found to contain both 2-bromoethyl tellurium bromide products, and upon subsequent heating of the reaction effluent at 150° C. for three hours under argon atmosphere, 2-bromoethyl acetate, ethylene glycol diacetate and 1,2-dibromoethane are found to be formed in yields of about 125 mole %, 17 mole % and 1.2 mole %, respectively, based on the moles of Te charged as the 2-bromoethyl tellurium bromide.

EXAMPLE 14

The procedure of Example 1, 3.5 parts of tellurium tetrabromide and 50 parts of ethanol are charged to the reaction vessel and are contacted at 25° C. for three hours with gaseous ethylene at atmospheric pressure. At the end of this reaction period, analysis of the reaction liquid shows bis (2-bromoethyl) tellurium dibromide and 2-bromoethyl tellurium tribromide to be present. The reaction liquid is then refluxed in an atmosphere of argon (400 psig) at a temperature of 80° C. for a period of two hours. At the end of this time, gas chromatographic analysis of the liquid mixture indicates the presence of 2-bromoethyl ethyl ether in a yield of about 124.6 mole % based on the moles of Te charged as the 2-bromoethyl tellurium bromide.

EXAMPLE 15

The procedure of Example 14 is repeated except that the reaction effluent, following the three hours of reaction time of the tellurium tetrabromide and ethanol to form the desired 2-bromoethyl tellurium bromide products, is subjected to a vacuum distillation using the method of Example 2, with the distillation being carried out to dryness. The solid residue (4 parts) thereby obtained is then heated in a separated vessel with an excess of glacial acetic acid (80 parts) at a temperature of 150° C. for three hours in an atmosphere of argon (400 psig). The liquid reaction mixture is analyzed by gas chromatography and is found to contain 2-bromoethyl acetate and ethylene glycol diacetate in yields of about 7.9 mole % and 175 mole %, respectively, based on the moles of Te charged as the 2-bromoethyl tellurium bromide.

EXAMPLE 16

The procedure of Example 14 is repeated in separate runs except that the organic solvents identified in Table II are employed instead of ethanol. At the conclusion of the initial three hour reaction time, a sample of each effluent is analyzed and is found to contain bis (2-bromoethyl) tellurium dibromide and 2-bromoethyl tellurium tribromide. The remainder of each effluent is then heated as in Example 14 to form the substituted ethylene products identified in Table II.

TABLE II

| Run No. | Organic Solvent | Substituted Ethane Product |
|---|---|---|
| 1 | propanol | 2-bromoethyl propyl ether |
| 2 | propionic acid | ethylene glycol dipropionate; 2-bromoethyl dipropionate |
| 3 | 2-bromoethanol | bis (2-bromoethyl) ether |
| 4 | aqueous HCl (20 wt. % HCl) | 1-chloro-2-bromoethane; 1,2-dichloroethane |

As will be apparent from the foregoing, the same liquid can function as an organic solvent for the reaction in the formation of 2-bromoethyl tellurium bromides of this invention and as the nucleophile source in reaction of these 2-bromoethyl tellurium bromides to form substituted ethane products in accordance with this invention.

It will be obvious that various changes and modifications may be made without departing from the invention and it is intended, therefore, that all matter contained in the foregoing description shall be interpreted as illustrative only and not limitative of the invention.

We claim:

1. Bis (2-bromoethyl) tellurium dibromide.
2. 2-Bromoethyl tellurium tribromide.
3. A process for preparing a 2-bromoethyl tellurium bromide selected from the group consisting of bis (2-bromoethyl) tellurium tribromide, 2-bromoethyl tellurium tribromide and mixtures thereof which comprises contacting ethylene with a source of tellurium tetrabromide in liquid medium in the presence of a polar organic solvent for the reaction which is inert under the conditions of the reaction, at a temperature of less than about 125° C. and in the substantial absence of molecular oxygen, to form the 2-bromoethyl tellurium bromide.
4. The process according to claim 3 wherein the reaction temperature is maintained at from about 10° to 80° C.
5. The process according to claim 3 wherein the source of tellurium tetrabromide comprises a member selected from the group consisting of tellurium tetrabromide, a mixture of tellurium dioxide and hydrobromic acid, and mixtures thereof.
6. The process of claim 3 wherein the organic solvent comprises a member selected from the group consisting of aliphatic, aromatic or heterocyclic mono- or polyethers of from 2 to 20 carbon atoms, alcohols of from 1 to 20 carbon atoms, aliphatic, alicyclic or aromatic sulfoxides and sulfones, amides of from 2 to 20 carbon atoms, nitriles of from 2 to 20 carbon atoms, aromatics of from 6 to 24 carbon atoms, esters of from 2 to 20 carbon atoms, alkanes of from 2 to 20 carbon atoms, aliphatic halogenated hydrocarbons of from 1 to 20 carbon atoms, halogenated aromatic hydrocarbons of from 6 to 24 carbon atoms, and carboxylic acids of from 1 to 20 carbon atoms.
7. The process according to claim 3 wherein the organic solvent comprises a member selected from the group consisting of aliphatic and aromatic nitriles of up to 7 carbon atoms, aliphatic and cycloaliphatic alcohols of up to B 6 carbon atoms, monocarboxylic acids of up to 6 carbon atoms, and aliphatic or aromatic ethers of up to 12 carbon atoms.

* * * * *